US012638442B2

(12) United States Patent
Ng

(10) Patent No.: US 12,638,442 B2
(45) Date of Patent: May 26, 2026

(54) THERMO-PLASMONIC BIOCHIP, MANUFACTURING METHOD THEREOF, BIOSENSING SYSTEM CONTAINING THE THERMO-PLASMONIC BIOCHIP, AND APPLICATION THEREOF

(71) Applicant: Rafael Biotechnology Company Limited, Hong Kong (CN)

(72) Inventor: Siu Pang Ng, Hong Kong (CN)

(73) Assignee: Rafael Biotechnology Company Limited, Hong Kong (CN)

( * ) Notice: Subject to any disclaimer, the term of this patent is extended or adjusted under 35 U.S.C. 154(b) by 880 days.

(21) Appl. No.: 17/931,769

(22) Filed: Sep. 13, 2022

(65) Prior Publication Data

US 2024/0044888 A1 Feb. 8, 2024

(30) Foreign Application Priority Data

Aug. 2, 2022 (CN) .......................... 202210921401.5

(51) Int. Cl.
*G01N 33/543* (2006.01)
*G01N 21/552* (2014.01)

(52) U.S. Cl.
CPC ..... *G01N 33/54373* (2013.01); *G01N 21/554* (2013.01)

(58) Field of Classification Search
CPC ....................... G01N 21/554; G01N 33/54373
See application file for complete search history.

(56) References Cited

U.S. PATENT DOCUMENTS

| | | | |
|---|---|---|---|
| 2006/0197952 A1 | 9/2006 | Chen et al. | |
| 2008/0093541 A1* | 4/2008 | Ando ................... | G01N 21/645 |
| | | | 356/246 |
| 2014/0004507 A1 | 1/2014 | Malic et al. | |

FOREIGN PATENT DOCUMENTS

| | | | | |
|---|---|---|---|---|
| CN | 112033932 A | * | 12/2020 | ............. G01N 21/55 |
| CN | 114018881 A | * | 2/2022 | ......... G01N 21/6402 |

* cited by examiner

*Primary Examiner* — Duane Smith
*Assistant Examiner* — Austin Q Le
(74) *Attorney, Agent, or Firm* — The Webb Law Firm

(57) ABSTRACT

A thermo-plasmonic biochip, a manufacturing method thereof, a biosensing system containing the thermo-plasmonic biochip and an application thereof are disclosed. The biochip includes a first component and a second component, substrates of which both include a recess, a plurality of flow cells arranged on a bottom surface of the recess at intervals, a conical waveguide longitudinally arranged in the flow cells, and TiN nanocubes arranged on a conical surface of the conical waveguide. The first component further includes a sample inlet hole and a sample outlet hole communicated with the recess; and composition materials of the first component and the second component contain crystal violet.

18 Claims, 17 Drawing Sheets

45nm TiN nanocube

PMMA substrate
with dipole
emitters

Probe beam adding 4.08 g of crystal violet powder to 1,180 g of transparent PMMA resin and fully stirring the mixture

 

performing 3D printing with a precision of 25 μm to obtain a first part performing 3D printing with a precision of 25 μm to obtain a second part

 

rinsing with a mixed solution of 90% ethanol +10% pure water for 15 minutes rinsing with a mixed solution of 90% ethanol +10% pure water for 15 minutes

 

heating up to 60℃ and curing with 365-nm ultraviolet light for 15 minutes heating up to 60℃ and curing with 365-nm ultraviolet light for 15 minutes

 

adding 100 μg/mL ethanol solution of TiN nanocubes to each conical waveguide adding 100 μg/mL ethanol solution of TiN nanocubes to each conical waveguide

 

drying with nitrogen drying with nitrogen

 

docking the first component with the second component to obtain TPLC assembly

FIG. 27

THERMO-PLASMONIC BIOCHIP, MANUFACTURING METHOD THEREOF, BIOSENSING SYSTEM CONTAINING THE THERMO-PLASMONIC BIOCHIP, AND APPLICATION THEREOF

CROSS-REFERENCE TO RELATED APPLICATION

This application claims priority to Chinese Patent Application No. 202210921401.5 filed Aug. 2, 2022, the disclosure of which is hereby incorporated by reference in its entirety.

BACKGROUND

Technical Field

The disclosure relates to the field of biosensing, and more particularly, to a thermo-plasmonic biochip, a manufacturing method thereof, a biosensing system containing the thermo-plasmonic biochip and an application thereof.

Technical Description

Surface Plasmon Resonance (SPR) biosensor monitors interactions between various biomolecules by using inherent characteristics of nanoparticles to analyze biological samples. At present, most surface plasmon resonance biosensors are usually based on silver, gold, or silver-gold alloy for the plasmonic supporting material to excite the collective oscillation of electron cloud. However, when using gold for the plasmonic supporting material, there are two issues that preclude the wide-spread usage of gold based SPR biosensor: (i) expensive raw material and (ii) precise thickness of the thin film to about 50 nm.

Moreover, existing SPR devices are also limited in the number of parallel detection channels. Even with the most advanced models offered by established manufacturer, e.g., Biacore® K8, Bruker® Sierra, Reichert® 4SPR, etc., which normally consists of four to eight channels, which is far from meeting the demand of high-throughput rapid detection of biological samples. The limited number of the detection channels in the SPR system is due to the use of Attenuated Total Reflection (ATR) configuration. When the ATR configuration is used, the incident angle needs to be adjusted to over 70 degrees, resulting in that the reflected image is too narrow to be focused with high fidelity, so it is very limited in applications. Due to the insufficient number of detection channels in the SPR system, the parallel processing ability of the SPR system is greatly limited, which cannot meet the demand of high-throughput rapid detection of the biological samples.

Therefore, there is an urgent need to provide a thermo-plasmonic biochip and a manufacturing method thereof, which can not only reduce the manufacturing cost and improve the detection accuracy, but also meet the demand of high-throughput rapid detection.

SUMMARY

The disclosure aims at solving at least one of the technical problems in the existing art. Therefore, the disclosure provides a thermo-plasmonic biochip, which has low manufacturing cost, high detection accuracy on the premise of ensuring the resolution, and can be used for the detection of fluidic samples to study intermolecular interactions.

The disclosure further provides a manufacturing method of the thermo-plasmonic biochip above.

The disclosure further provides a biosensing system including the thermo-plasmonic biochip above.

The disclosure further provides an application of the thermo-plasmonic biochip above or the biosensing system above in studying intermolecular interactions.

According to a first aspect of the disclosure, a thermo-plasmonic biochip is provided, including:

a first component, including a first substrate, wherein the first substrate is provided with a sample inlet hole, a first recess and a sample outlet hole which are communicated in sequence, a bottom surface of the first recess is provided with a plurality of first flow cells at intervals, each first flow cell is internally provided with a longitudinally arranged first conical waveguide extending out of the first flow cell and located in the first recess, and a plurality of titanium nitride nanocubes are arranged on a conical surface of the first conical waveguide through chemical bonds;

a second component, including a second substrate, wherein the second substrate is provided with a second recess, a bottom surface of the second recess is provided with a plurality of second flow cells at intervals corresponding to the first flow cells, each second flow cell is internally provided with a longitudinally arranged second conical waveguide corresponding to the first conical waveguide, the second conical waveguide extends out of the second flow cell and is located in the second recess, and a plurality of titanium nitride nanocubes are arranged on a conical surface of the second conical waveguide through chemical bonds; and wherein composition materials of the first substrate, the second substrate, the first conical waveguide and the second conical waveguide contain crystal violet.

In some embodiments of the disclosure, the composition materials of the first substrate, the second substrate, the first conical waveguide and the second conical waveguide contain the crystal violet.

In some embodiments of the disclosure, the first substrate and the second substrate allow light with a wavelength of 400 nm to 1000 nm to pass through. Under the excitation of light in the above wavelength range, the crystal violet (CV) molecules in the PMMA can be used as dipole sources of the TiN nanocubes to produce the thermo-plasmonic effect.

In some embodiments of the disclosure, the first substrate and the second substrate allow light with a wavelength of 500 nm to 800 nm to pass through.

In some embodiments of the disclosure, the first substrate and the second substrate allow light with a wavelength of 550 nm to 650 nm to pass through.

In some embodiments of the disclosure, the first substrate and the second substrate allow light with a wavelength of 590 nm to pass through.

In some embodiments of the disclosure, heights of the first conical waveguide and the second waveguide are independently selected from 300 µm to 700 µm, respectively.

In some embodiments of the disclosure, the heights of the first conical waveguide and the second waveguide are independently selected from 400 µm to 600 µm, respectively.

In some embodiments of the disclosure, the heights of the first conical waveguide and the second waveguide are independently selected from 450 µm to 550 µm, respectively.

In some embodiments of the disclosure, the heights of the first conical waveguide and the second waveguide are 500 µm.

In some embodiments of the disclosure, diameters of bottom surfaces of the first conical waveguide and the second waveguide are independently selected from 100 μm to 300 μm, respectively.

In some embodiments of the disclosure, the diameters of the bottom surfaces of the first conical waveguide and the second waveguide are independently selected from 125 μm to 250 μm, respectively.

In some embodiments of the disclosure, the diameters of the bottom surfaces of the first conical waveguide and the second waveguide are 125 μm.

In some embodiments of the disclosure, a distance between tips of the first conical waveguide and the corresponding second conical waveguide is less than 5 μm.

In some embodiments of the disclosure, sizes of the first titanium nitride nanocube and the second titanium nitride nanocube are independently selected from 45 nm to 65 nm, respectively.

In some embodiments of the disclosure, the size of the titanium nitride nanocube is 45 nm.

In some embodiments of the disclosure, an amount of the crystal violet is 500 to 600,000 crystal violet molecules per cubic micron of the PMMA.

In some embodiments of the disclosure, the amount of the crystal violet is 70,000 to 85,000 crystal violet molecules per cubic micron of the PMMA.

In some embodiments of the disclosure, the amount of the crystal violet is 70,000 to 80,000 crystal violet molecules per cubic micron of the PMMA.

In some embodiments of the disclosure, the plurality of first flow cells are distributed in an array.

In some embodiments of the disclosure, the number of the first flow cells is 1 to 300. Different first flow cells and the corresponding second flow cells thereof may be used to monitor interactions between biomolecules of the same type in the same fluidic sample, and may also be used to monitor interactions between biomolecules of different type in the same fluidic sample.

In some embodiments of the disclosure, the number of the first flow cells is 100 to 200.

In some embodiments of the disclosure, the number of the first flow cells is 144. The arrangement of the first flow cells is 12×12.

In some embodiments of the disclosure, the biochip further includes a fastening structure for fastening the first substrate and the second substrate to fix the first conical waveguide relative to the second conical waveguide.

In some embodiments of the disclosure, the fastening structure includes a positioning hole and a positioning wedge. The positioning hole is arranged on the first substrate, and the positioning wedge is arranged on the second substrate.

In some embodiments of the disclosure, cross section of the positioning wedge may be triangular, trapezoidal, V-like, U-shaped or rectangular. It may be understood that those having ordinary skills in the art can choose a shape that can be used to fix the first flow cell relative to the corresponding second flow cell thereof as the shape of the cross section of the positioning wedge, so as to facilitate detection.

In some embodiments of the disclosure, multiple positioning holes are provided.

In some embodiments of the disclosure, when multiple positioning holes are provided, shapes of different positioning holes are the same or different.

According to a second aspect of the disclosure, a manufacturing method of the thermo-plasmonic biochip according to the first aspect of the disclosure is provided, including:

S1: generating the first component and the second component which are not modified with the titanium nitride nanocubes by using the composition materials;

S2: dispersing and fixing the titanium nitride nanocubes on the conical surfaces of the first conical waveguide and the second conical waveguide respectively to obtain the first component and the second component; and S3: docking the first component with the second component.

In some embodiments of the disclosure, step S1 is realized by 3D printing and UV curing.

In some embodiments of the disclosure, in step S2, the titanium nitride nanocubes are dispersed and fixed on the conical surfaces of the first conical waveguide and the second conical waveguide by wet chemical method.

According to a third aspect of the disclosure, a biosensing system containing the thermo-plasmonic biochip according to the first aspect of the disclosure is provided.

According to a fourth aspect of the disclosure, an application of the thermo-plasmonic biochip according to the first aspect of the disclosure or the biosensing system according to the third aspect of the disclosure is provided.

In order to excite plasmonic resonance, it requires the real part of dielectric function of the plasmonic supporting material has to be negative and the imaginary part of dielectric function has to be as small as possible to reduce damping of electron oscillation. As shown in FIG. 1, the real parts of the dielectric functions of four commonly employed plasmonic supporting materials-gold (Au), silver (Ag), copper (Cu) and aluminum (Al)-at 400 nm to 900 nm are negative. As shown in FIG. 2, when the wavelength is the same, the silver has the smallest imaginary part among the gold, the silver, the copper and the aluminum.

Typical thermo-plasmonic effects arise when illuminating a single or an ensemble of plasmonic nanoparticles with light in order to generate heat and locally rise the particle's and medium's temperature. This is due to light-matter interaction in nanometer scale. Given dielectric function of the material, the optical response of the nanostructure to incident light can be calculated via the Maxwell's equation. The time-averaged absorbed optical power $Q_{abs}$ can be expressed as:

$$Q_{abs} = -\frac{1}{2}\mathrm{Re}\left\{\int\int_S [E_{tot} \times H_{tot}^*] \cdot n dS\right\};$$ (equation I)

wherein, Re refers to the real part, $E_{tot}$ and $H_{tot}^*$ are the total electric field and the conjugate complex total magnetic field experienced by the nanoparticle, n is a vertical unit vector, and S is the surface enclosed the nanoparticle.

With monochromatic illumination, the calculation equation of $Q_{abs}$ may be further simplified as:

$$Q_{abs} = \frac{\omega}{2}\mathrm{Im}\{\varepsilon\}\int\int\int |E|^2 dV;$$ (equation II)

wherein, ω is the angular frequency of the incident wavelength, $\mathrm{Im}\{\varepsilon\}$ is the imaginary part of the dielectric function of the nanoparticle, |E| is the total electric field amplitude, dV is the nanoparticle volume, and the integration is done on the nanoparticle volume.

It can be seen that $Q_{abs}$ is proportional to the imaginary part of the dielectric function of the material, that is, the larger the imaginary part of the dielectric function, the higher the $Q_{abs}$, and the greater the ability of nanoparticles to generate heat through Joule effect of electromagnetic field. It can be seen from FIG. 2 that the imaginary part of the dielectric function of the silver is nearly zero, so the $Q_{abs}$ thereof is negligible; the imaginary parts of the imaginary dielectric functions of the gold and the copper are very small, so the $Q_{abs}$ of the two is also very small. However, the aluminum may be oxidized into alumina immediately when contacting air, thus losing metal properties, so aluminum is not suitable for practical operation. Therefore, none of the silver, the gold, the copper and the aluminum are suitable for thermo-plasmonic applications.

The real part and the imaginary part of the dielectric function of the titanium nitride (TiN) are shown in FIG. 3 and FIG. 4, respectively. As can be seen from FIG. 3 that, the real parts of the dielectric functions of two TiNs reported in the existing art are both less than 0 at 500 nm to 900 nm, wherein, at the same wavelength, the imaginary part of the dielectric function of the TiN reported by Naik et al. (TiN Naik (2012)) is comparable to gold, and the imaginary part of the dielectric function of the TiN reported by Judek et al. (TiN Judek (2021)) is significantly larger than gold. This indicates that the absorbed power (i.e., $Q_{abs}$) by TiN nanoparticle is higher than gold, and the TiN nanoparticle is more suitable for thermo-plasmonic applications.

The reference document of TiN Naik (2012) is "Naik G V, Schroeder J L, Ni X, et al. Titanium nitride as a plasmonic material for visible and near-infrared wavelengths [J]. Optical Materials Express, 2010, 2(4):478-489"; and the reference document of TiN Judek (2021) is "Judek Jaroslaw, Wrobel Piotr, Michalowski Pawel Piotr et al. Titanium Nitride as a Plasmonic Material from Near-Ultra-violet to Very-Long-Wavelength Infrared Range. [J].Materials (Basel), 2021, 14: undefined".

The resolution of the titanium nitride is about $2\times10^{-7}$ refractive index unit (RIU), which is almost the same as those of gold nanoislands (AuNIs) or gold-silver bimetal nanoislands (BMNIs). The TiN thin film was further modi-fied in combination with sacrificial thermal dewetting tem-plates to create TiN nanoholes on glass. LSPR biosensing with TiN nanoholes achieved resolution to $9\times10^{-8}$ RIU which is equivalent to those of AuNIs and BMNIs. Besides, functionalization of TiN is straightforward with biotinylated antibody so it reduces the number of chemicals involved in comparison with gold and improve the detection accuracy. To sum up, using the titanium nitride instead of the gold can not only achieve basically the same resolution, but also further reduce the manufacturing cost of the plasmonic biochip and improve the detection accuracy of fluidic samples.

The light with a wavelength of 590 nm can excite a crystal violet fluorophore, and further excite the thermo-plasmonic effect of the TiN nanocubes in a near field, resulting in instantaneous local heating, thus improving the binding affinity between a receptor (referring to the biomolecules fixed on the TiN nanocube in advance) and a target (referring to the biomolecules in the detected samples).

The disclosure has the beneficial effects as follows.

The refractive index resolution of the thermo-plasmonic biochip provided by the disclosure is $1.6\times10^{-9}$ RIU. The detection limit is lowered to a level of fg/mL, and the detection accuracy is high. The volume of the fluidic sample required for detection is small. The manufacturing cost is low. Compared with the conventional PCR reaction detec-tion, the biochip provided by the disclosure has lower energy consumption, which is about 1/250 of the conventional PCR reaction, and is much more environmentally friendly.

The manufacturing method of the thermo-plasmonic biochip provided by the disclosure has simple steps and low requirements for those having ordinary skills in the art, and is easy to realize.

BRIEF DESCRIPTION OF THE DRAWINGS

The disclosure will be further explained with reference to the accompanying drawings and embodiments hereinafter, wherein:

FIG. 27 is a schematic flowchart of manufacturing a biochip according to the disclosure;

DETAILED DESCRIPTION

Figure 1:
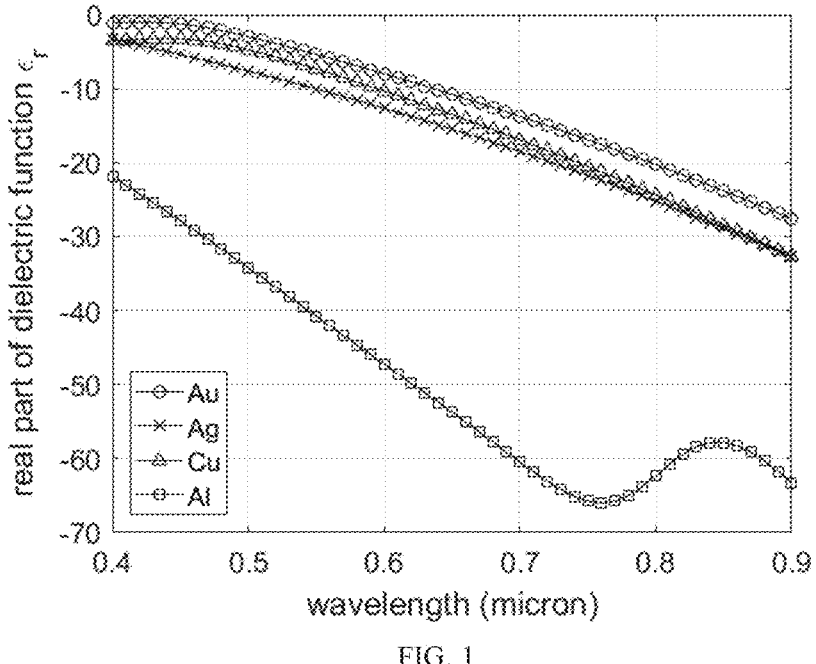
FIG. 1 shows the real part ($\varepsilon_r$) of the dielectric function of various metal elements commonly found in SPR biosensors in the existing art.
Figure 2:
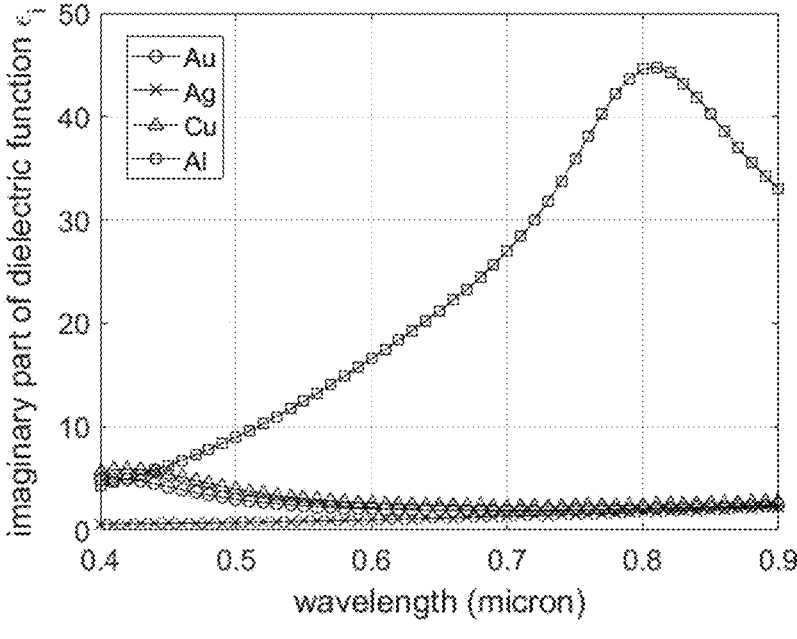
FIG. 2 shows the imaginary part ($\varepsilon_i$) of the dielectric function of various metal elements commonly found in SPR biosensors in the existing art.
Figure 3:
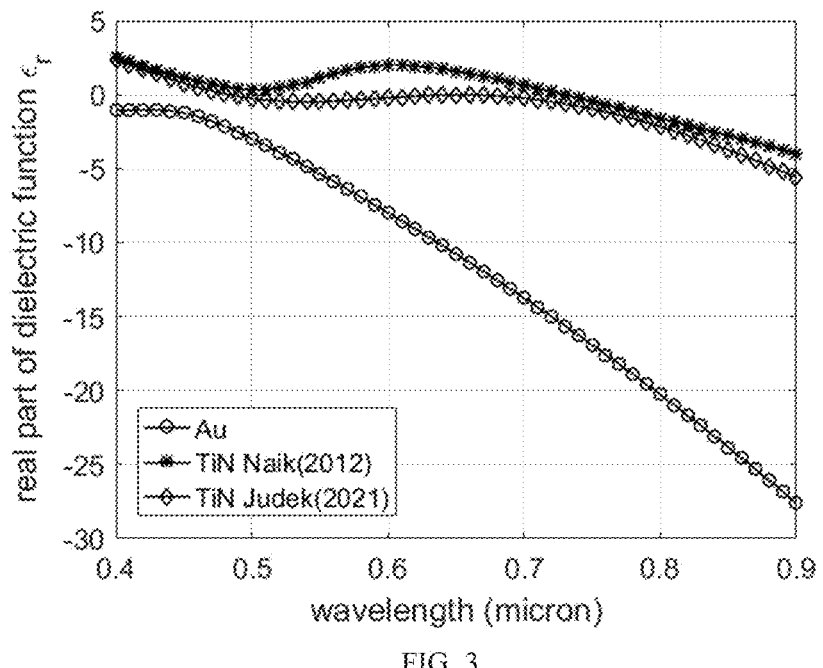
FIG. 3 shows the real part of the dielectric function of gold and titanium nitride thin films in the existing art.
Figure 4:
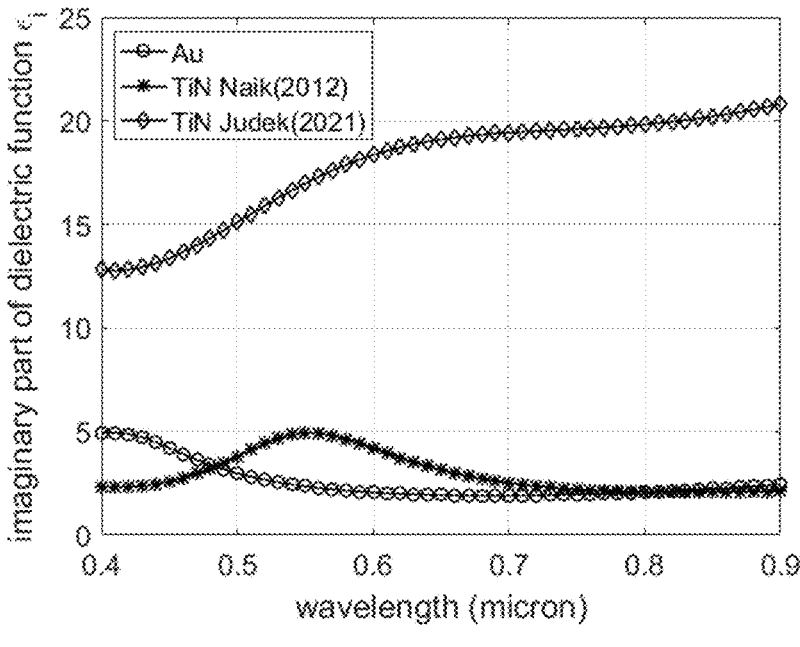
FIG. 4 shows the imaginary part of the dielectric function of the gold and titanium nitride thin films in the existing art.

In order to make the technical solutions of the disclosure clearer to those having ordinary skills in the art, the following embodiments are listed for explanation. It should be noted that the following embodiments do not limit the scope of protection claimed by the disclosure.

The embodiments of the disclosure will be described in detail below. The embodiments described below with reference to the accompanying drawings are exemplary and are only intended to explain the disclosure, but should not be construed as limiting the disclosure.

In the description of the disclosure, it should be understood that several means one or more, multiple means more than two, and greater than or less than is understood as excluding this number. If there is a description to the first and second, it is only for the purpose of distinguishing between technical features, and shall not be understood as indicating or implying relative importance, implicitly indicating the number of the indicated technical features or implicitly indicating the order of the indicated technical features.

In the description of the disclosure, it should be noted that unless otherwise explicitly defined, words such as setting, installing, connecting and communicating should be understood in a broad sense, and those having ordinary skills in the art can reasonably determine the specific meanings of the above words in the disclosure in combination with the specific contents of the technical solutions.

Unless otherwise indicated, the reagents, methods, and devices employed in the disclosure are routine reagents, methods, and devices in the art. The test methods without specific experimental conditions in the following embodiments are usually performed in accordance with the conventional experimental conditions or the experimental conditions suggested by the manufacturer.

In the following embodiments, to solve the Maxwell equation and compute the thermoplasmonic effect, we employed the open-sourced finite-difference time-domain (FDTD) package MEEP. The dielectric function of TiN was adopted from TiN Judek (2021), and the parameters were converted into Drude-Lorentz model for calculation according to MEEP document (https://meep.readthedocs.io/en/latest/Scheme_Tutorial sNIaterial Di spersion/).

Crystalline violet (CV) was premixed with the methyl methacrylate (MMA) monomers, and then cured with 365 nm ultraviolet light for 15 minutes to obtain polymethylmethacrylate (PMMA) mixed with CV. According to CV concentration (the number of CV molecules per liter of PMMA), materials CV 1E-3M and CV 1E-4M with CV concentrations of $6.022 \times 10^{30}$/L and $6.022 \times 10^{19}$/L were obtained, respectively. Since the CV does not react with the MMA monomers and assuming even distribution, it means approximately 600,000 and 60,000 CV molecules per cubic micrometer (u m$^3$) of PMMA. TiN nanocubes were embedded in the surfaces of the PMMA without CV, the CV 1E-3M and the CV 1E-4M with CV respectively by wet chemical method. A suitable laser pumping source was selected based on the above materials and different sizes of TiN nanocubes.

Figure 5:
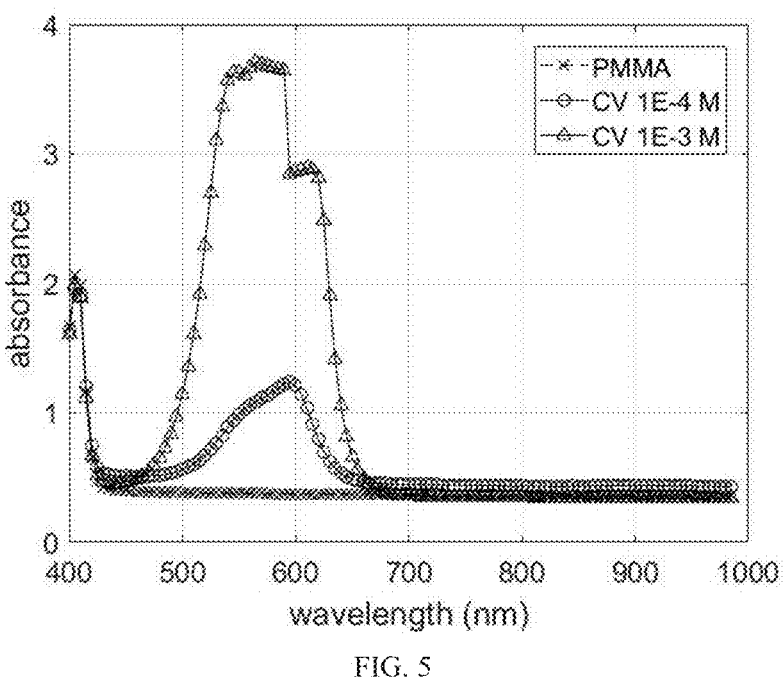
FIG. 5 shows ultraviolet-near infrared (UV-NIR) absorp-tion spectra of PMMA, CV 1E-4M and CV 1E-3M provided by an embodiment of the disclosure.

It can be seen from FIG. 5 that the UV-NIR absorbance peak of CV is approximately 590 nm, while the PMMA has no UV-NIR absorbance peak in a range of 500 nm to 700 nm. An amber LED emitting at 590 nm is selected to excite the CV molecules in the PMMA.

Figure 6:
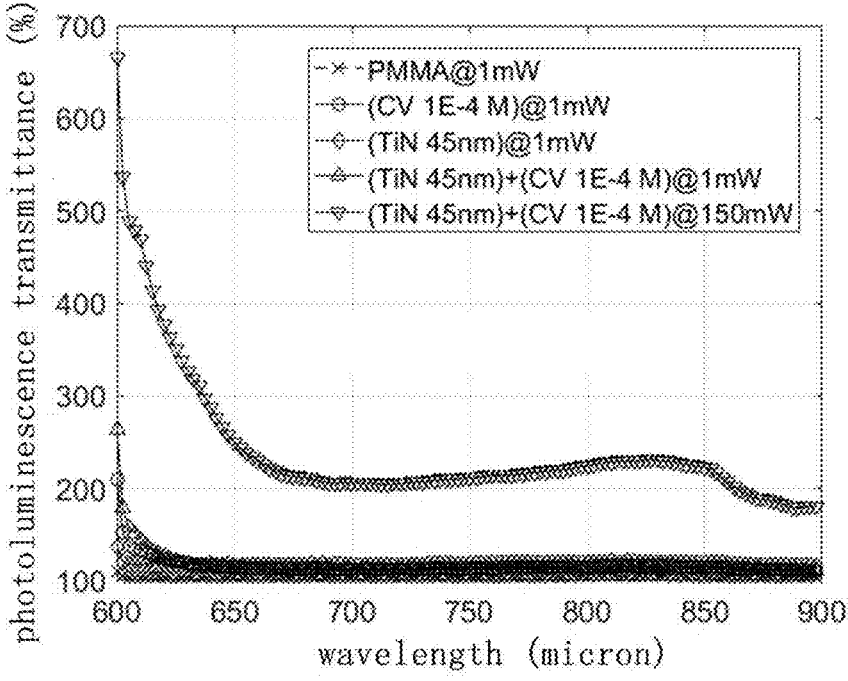
FIG. 6 shows photoluminescence spectra (PL) of the PMMA, the CV 1E-4M, and a dye with CV 1E-4M and modified by TiN nanocube excited at 590 nm.

It can be seen from FIG. 6 that the photoluminescence transmittance of the PMMA remains 100%, which is almost negligible. However, the photoluminescence transmittance of the material CV 1E-4M with CV exceeds 100% in a range of 600 nm to 650 nm, which shows obvious luminescence. The 45 nm TiN nanocube itself also has photoluminescence ability, and the photoluminescence phenomenon is more obvious especially when the 45-nm TiN nanocube is combined with the CV 1E-4M. When the power of the 590 nm excitation LED light source is increased from 1 mW to 150 mW, the photoluminescence wavelengths are obviously concentrated in the range of 600 nm to 650 nm.

Figure 7:
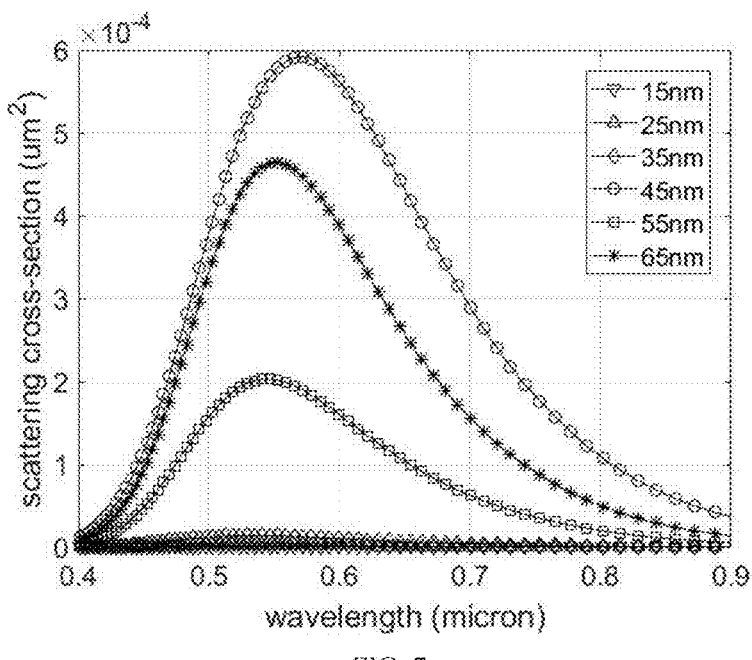
FIG. 7 shows a UV-NIR scattering cross section of TiN nanocubes with sizes of 15 nm, 25 nm, 35 nm, 45 nm, 55 nm and 65 nm in ethanol dispersion.

It can be seen from FIG. 7 that the 45-nm TiN nanocube has the largest scattering area and the strongest interaction with 400 nm to 900 nm electromagnetic waves, so the 45 nm TiN nanocube is used for simulation calculation and biological experiment.

The emission peak of the CV dye is about 638 nm, and the full-width-half-maximum (FWHM) of emission covers 610 to 700 nm. This is well covered by the LSPR extinction spectra of 45 nm TiN nanocubes.

The excitation of thermo-plasmonic effect usually demands laser pumping source. The pumping laser has to overlapped with the LSPR extinction peak to maximize the absorbed power of the nanoparticle. Therefore, the CV molecules can be used as suitable dipole sources for the TiN nanocubes of 45 nm to 65 nm to excite the near-field thermo-plasmonic effect.

Figure 8:
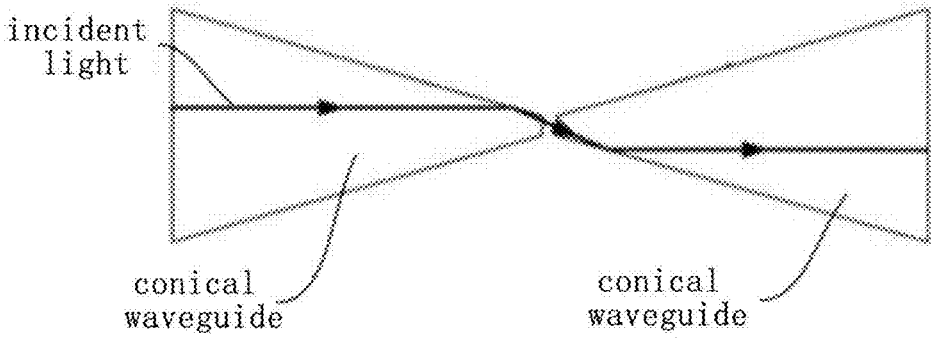
FIG. 8 shows an optical path diagram of light entering and exiting in two conical tip-to-tip waveguides.
Figure 9:
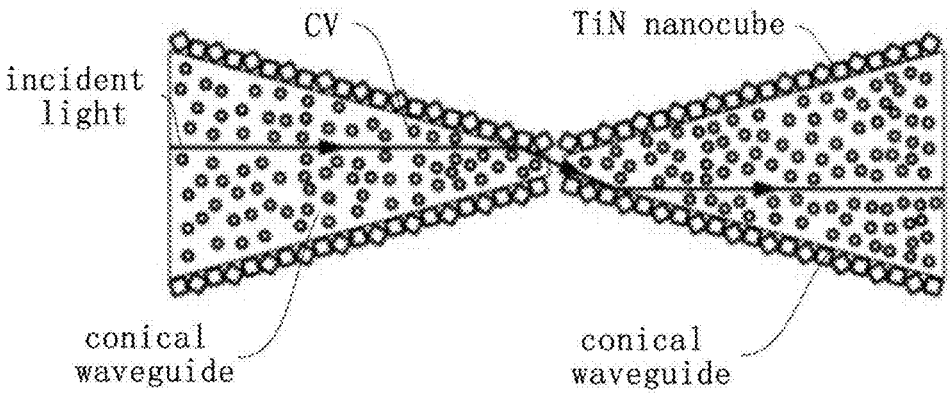
FIG. 9 shows an optical path diagram of light entering and exiting in two conical tip-to-tip waveguides doped with crystal violet and modified by TiN nanocubes provided by the embodiment of the disclosure.

In order to further improve the thermo-plasmonic and biosensing efficiency, a conical tip-to-tip waveguide design is provided in the disclosure. As shown in FIG. 8 and FIG. 9, the tips of the two conical waveguides face each other, and incident light traverses the conical waveguides by double reflection. Those having ordinary skills in the art should understand that the optical path diagram is only used to show a path of the incident light in the optical waveguide, and does not limit the incident direction of the light. The light may also be incident from the right and emitted from the left.

Figure 10:
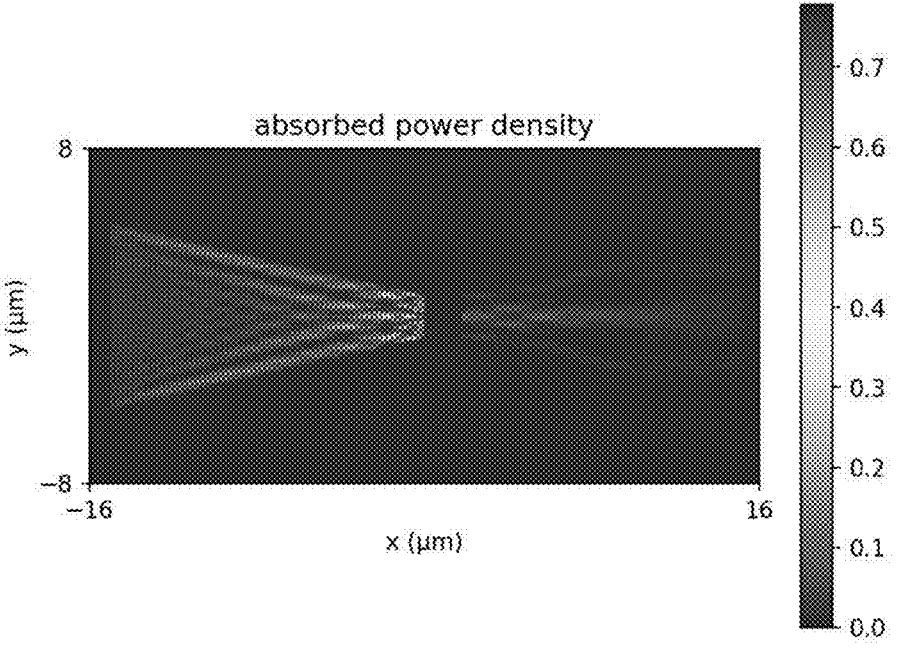
FIG. 10 shows electric field intensity distribution of two conical tip-to-tip waveguides on transmission of 638 nm probe laser plane wave computed by FDTD.
Figure 11:
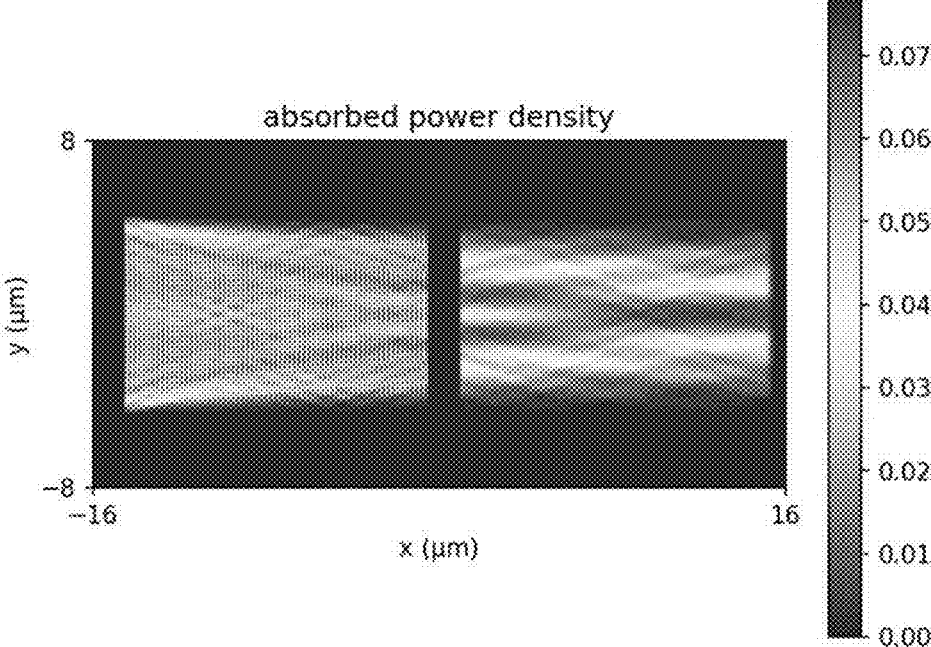
FIG. 11 shows electric field intensity distribution of two straight tip-to-tip waveguides on transmission of 638 nm probe laser plane wave computed by FDTD.

Absorbed power densities (APD) of the conical waveguide and the square waveguide are computed by FDTD. As shown in FIG. 10 and FIG. 11, an incident beam enters the optical waveguide from the left and propagates towards the right. With identical input source, the APD of the conical waveguide is higher than that of the straight waveguide by one order of magnitude. The incident beam demonstrates multiple reflections on the inclined surfaces of the conical waveguide, and it is further confined at the tip. On the other hand, the straight waveguide shows much less reflection and virtually no confinement.

The electric near-field distribution and absorbed power density of the 45-nm TiN nanocubes are computed by FDTD to determine the effect of emitting CVs on the anchored TiN nanocubes.

Figure 12:
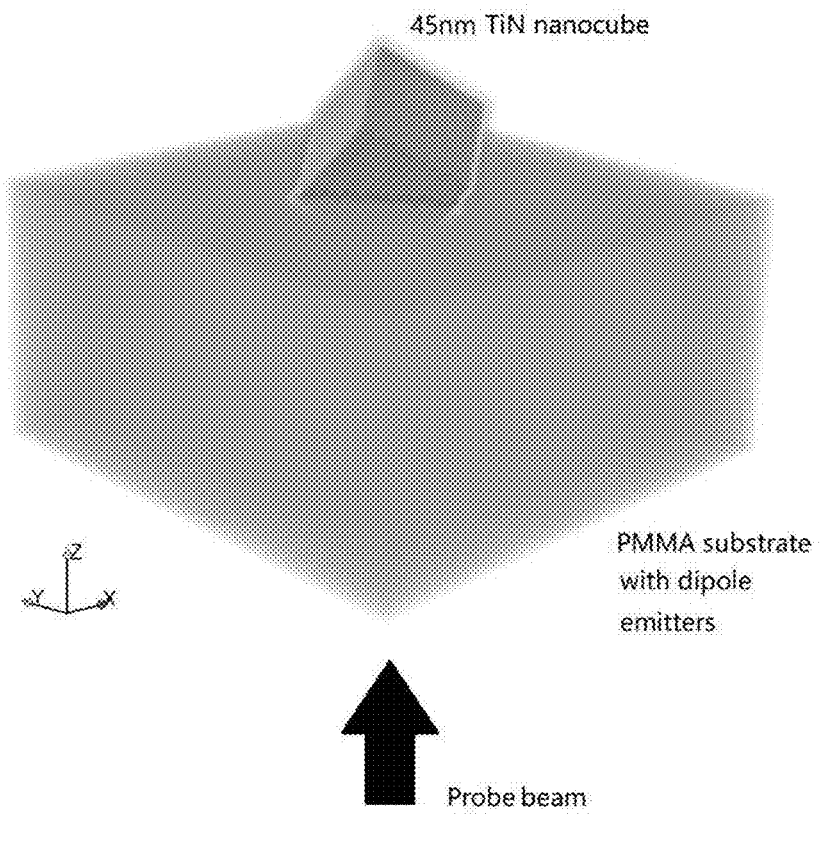
FIG. 12 shows a 3D model of a PMMA substrate with TiN nanocubes (45 nm) embedded in a surface computed by FDTD.

The CVs are represented by dipoles embedded in the PMMA substrate with Gaussian pulse emission. The dipole emission is centered at 638 nm and the full-width-half-maximum (FWHM) of emission covers 610 to 700 nm. The dipole sources are constructed with random initial phase and position within the PMMA substrate. Such configuration represents an ensemble of spontaneously recombining excitons and produces incoherent emission. Polarization of the dipoles are deliberately selected to be orthogonal to the incident probe beam which enters from bottom of the model. The probe beam is represented by a broad Gaussian pulse centered at 640 nm with FWHM spanning from 340 to 940 nm. The polarization of the probe beam is along the y-direction, thus the polarization of the dipole sources is along the x-direction. A discrete Fourier transform (DFT) field monitor is placed along the YZ plane at the cross-section of the TiN nanocubes. It is chosen to fully capture the relevant field data as the electromagnetic radiations of dipoles and probe beam propagate. As shown in FIG. 12, the dimensions of the model used for the above test are selected as follows. The substrate dimensions are 0.8×0.8×0.2 micron, the dimension of the TiN nanocube is 45 nm. The entire model occurs 0.8×0.8×0.8 micron (i.e., 800 nm in the XYZ directions) with spatial resolution of 2 nm and the simulation runtime is configured to be 100 periods of the maximum wavelength. This is done to ensure that sufficient cycles are collected by the DFT monitor for field data processing.

The resultant electric field in the YZ plane are shown in FIG. 13 to FIG. 17 ($|E_y|^2$ represents the time-average absolute electric field intensity). The number of the dipoles in the PMMA substrate is 0, 10 100, 1000, 10,000 respectively. As the number of dipoles increases, the absolute electric field intensity increases.

Figure 13:
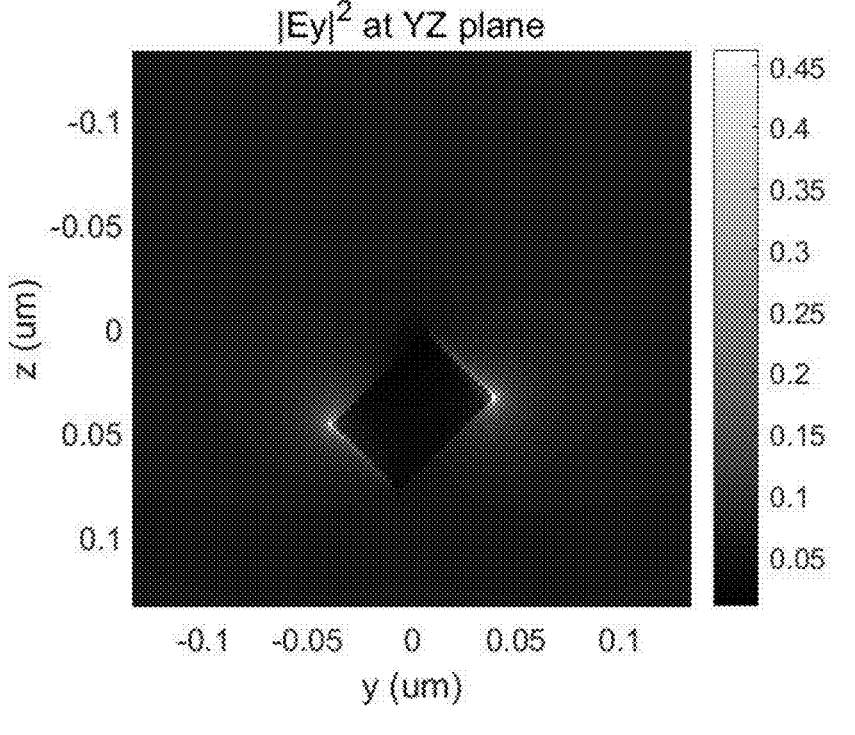
FIG. 13 shows the electric field intensity of the TiN nanocubes (45 nm) computed by FDTD when the 3D model shown in FIG. 12 does not contain dipoles.

When the number of the dipoles in the PMMA substrate is 0, the maximum absolute electric field intensity $E_y$ is 0.45 with default incident $E_y$ intensity set to 1.0. With incident polarization along the Y axis, the maximum electric field intensity is found at corners in the utmost Y directions, as shown in FIG. 13.

Figure 14:
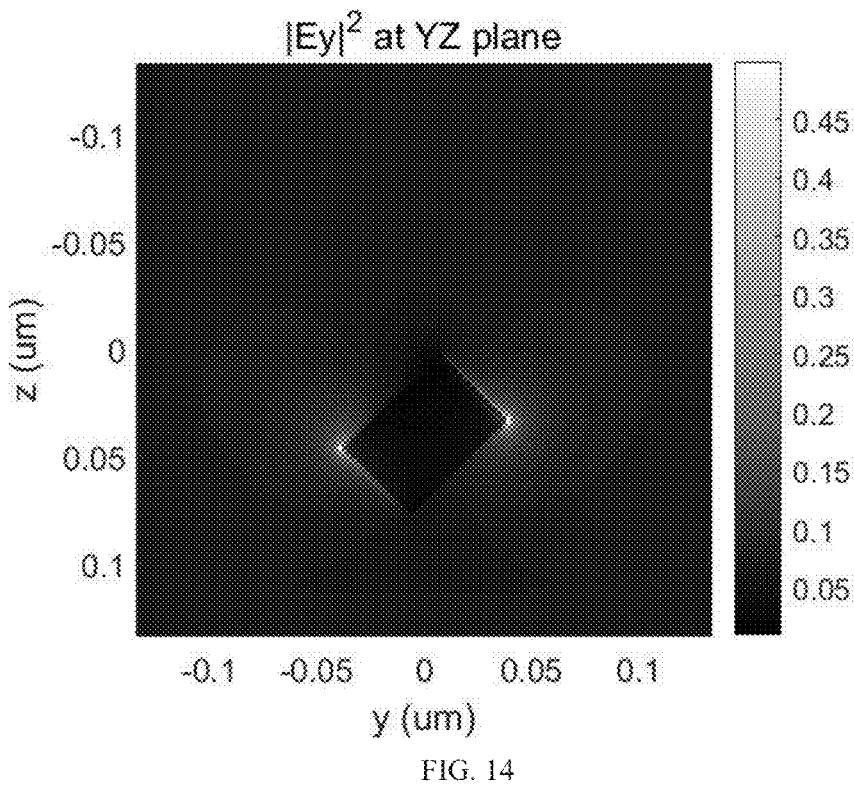
FIG. 14 shows the electric field intensity of the TiN nanocubes (45 nm) computed by FDTD when the 3D model shown in FIG. 12 contains 10 dipoles.

When the number of the dipoles in the PMMA substrate is 10, the maximum absolute electric field intensity is about 0.45, which is similar to that without dipoles, as shown in FIG. 14.

Figure 15:
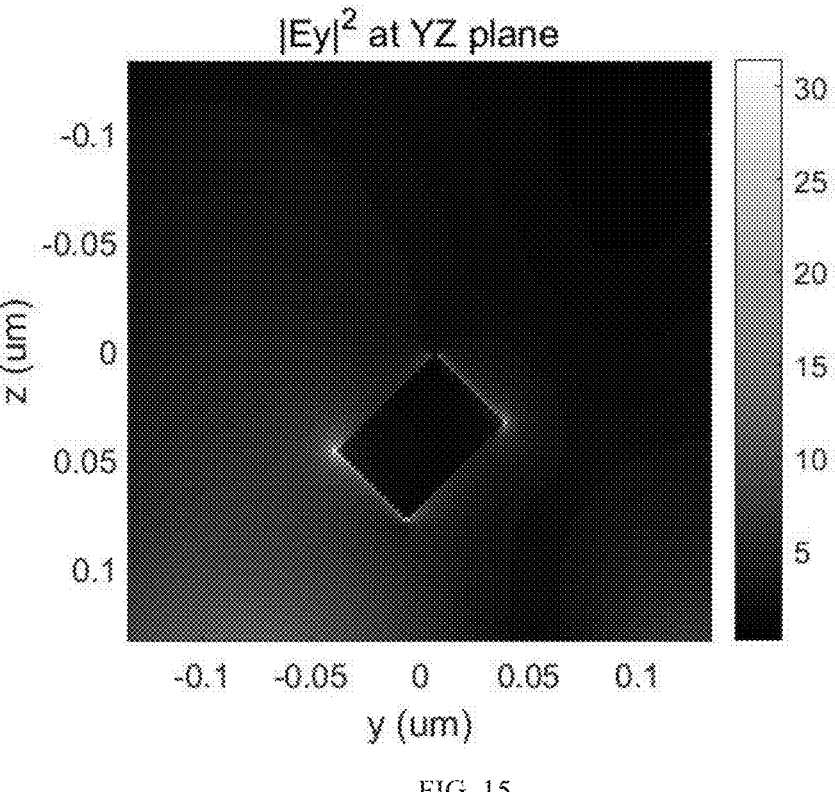
FIG. 15 shows the electric field intensity of the TiN nanocubes (45 nm) computed by FDTD when the 3D model shown in FIG. 12 contains 100 dipoles.

When the number of the dipoles in the PMMA substrate is 100, the maximum absolute electric field intensity is over 30, which is 66 times higher than that without dipoles, as shown in FIG. 15.

Figure 16:
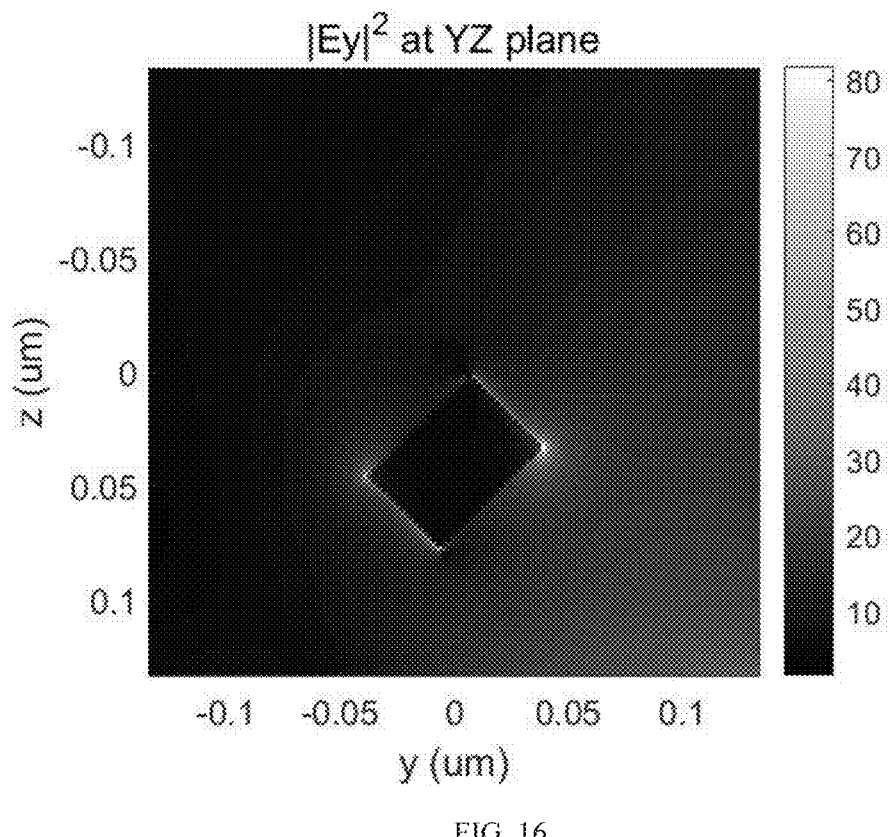
FIG. 16 shows the electric field intensity of the TiN nanocubes (45 nm) computed by FDTD when the 3D model shown in FIG. 12 contains 1,000 dipoles.

When the number of the dipoles in the PMMA substrate is 1,000, the maximum absolute electric field intensity is over 80, which is 177 times higher than that without dipoles, as shown in FIG. 16.

Figure 17:
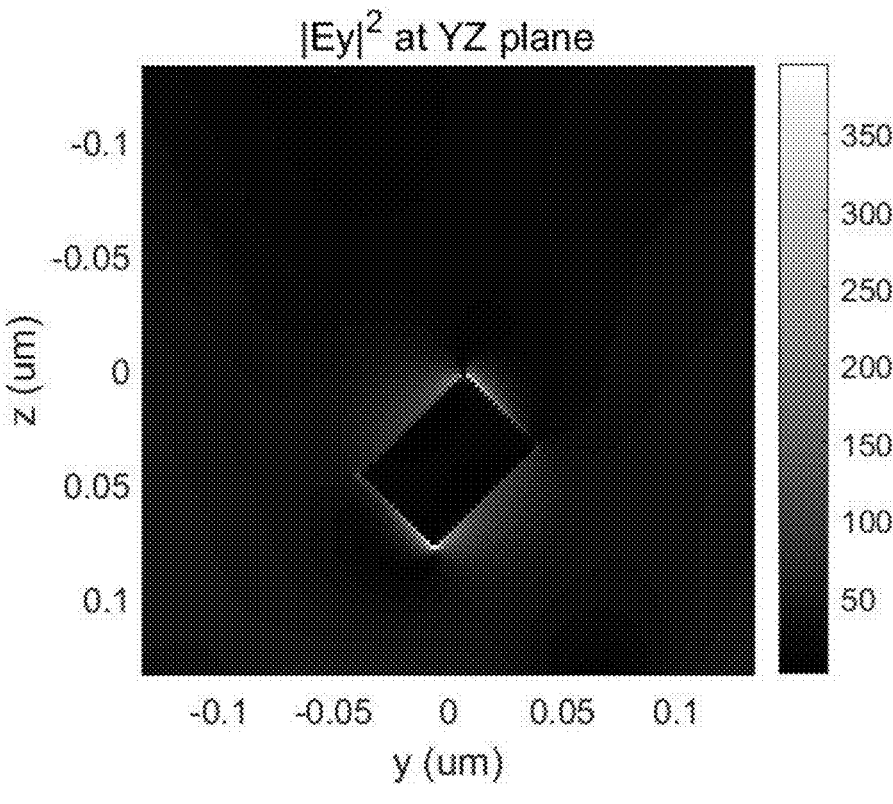
FIG. 17 shows the electric field intensity of the TiN nanocubes (45 nm) computed by FDTD when the 3D model shown in FIG. 12 contains 10,000 dipoles.

When the number of the dipoles in the PMMA substrate is 10,000, the maximum absolute electric field intensity is over 350, which is 750 times higher than that without dipoles, as shown in FIG. 17. In this case, there are about 78,000 CV molecules per cubic micron of the PMMA. The maximum absolute electric field intensity is found at corners in the utmost Z directions. All dipoles are X-polarized (oscillating in and out of the observation plane) and it improves light-matter interaction in the Z direction.

The absorbed power density of the TiN nanocube in the YZ plane is as shown in FIG. 18 to FIG. 22. The number of the dipoles in the PMMA substrate is 0, 10, 100, 1000 and 10,000, respectively. As the number of dipoles increases, the APD increases.

Figure 18:
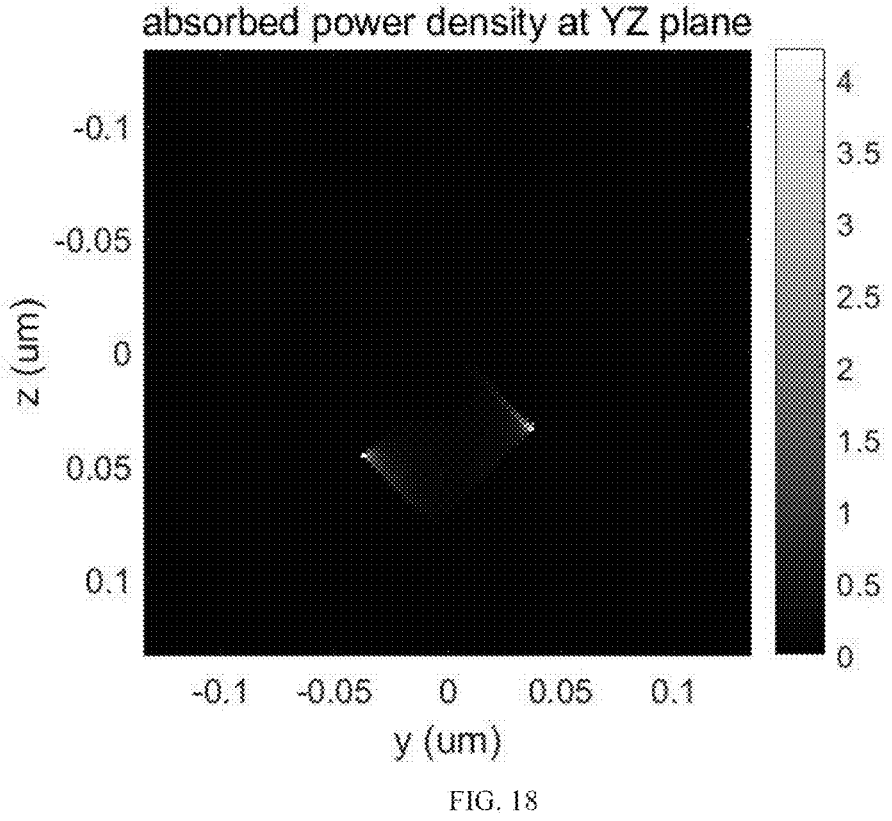
FIG. 18 shows the absorbed power density of the TiN nanocubes (45 nm) computed by FDTD when the 3D model shown in FIG. 12 does not contain dipoles.
Figure 19:
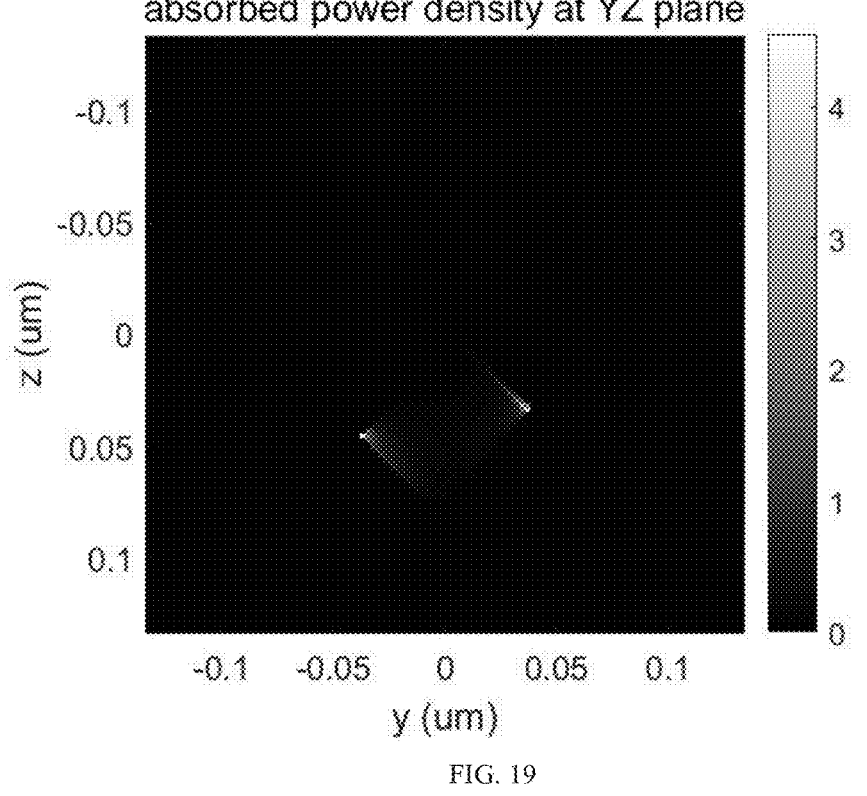
FIG. 19 shows the absorbed power density of the TiN nanocubes (45 nm) computed by FDTD when the 3D model shown in FIG. 12 contains 10 dipoles.

As shown in FIG. 18, with incident power of unity, the TiN nanocube amplifies the APD to about four times at the utmost Y corners and coincides with the maximum electric field intensity. In comparison to the optical designs in FIG. 10, the TiN nanocube has further increased the APD by 6 times over the conical waveguide alone and 60 times over the straight waveguide.

Figure 20:
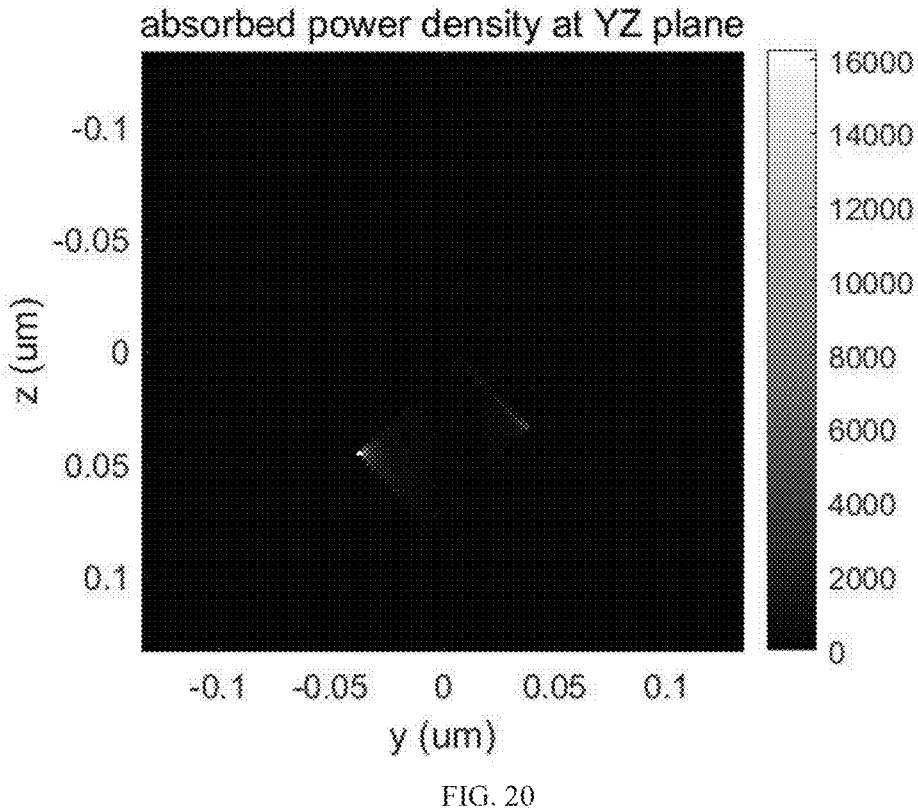
FIG. 20 shows the absorbed power density of the TiN nanocubes (45 nm) computed by FDTD when the 3D model shown in FIG. 12 contains 100 dipoles.

When the number of the dipoles in the PMMA substrate is 10, the APD attains 4, which is similar to the APD without dipoles, as shown in FIG. 20.

When the number of the dipoles in the PMMA substrate is 100, the APD attains 80,000, which is $2\times10^4$ times higher than that without dipoles, as shown in FIG. 20.

Figure 21:
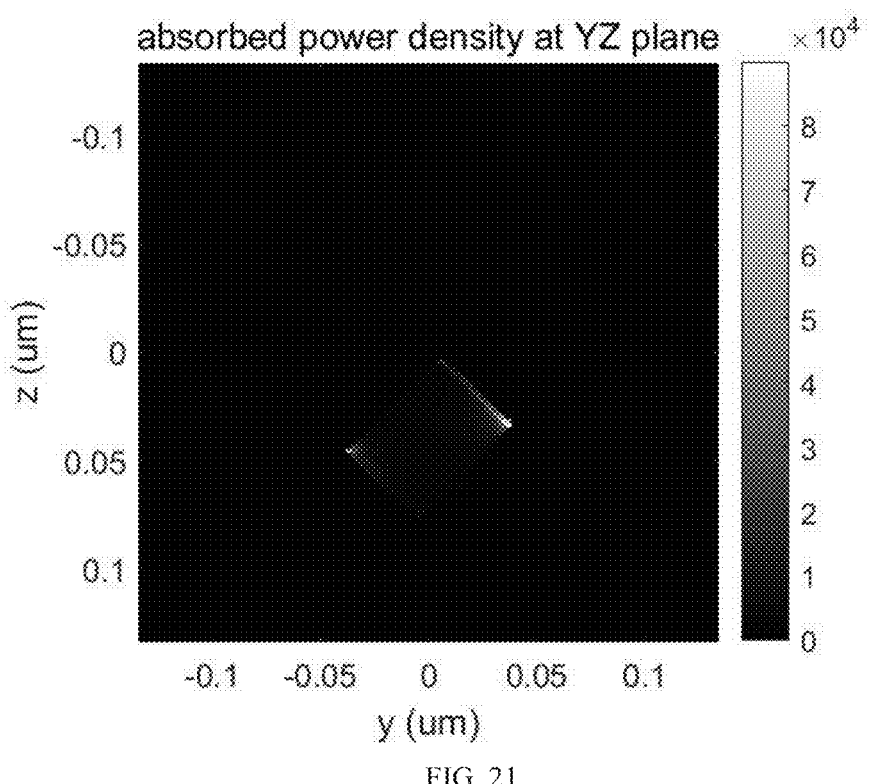
FIG. 21 shows the absorbed power density of the TiN nanocubes (45 nm) computed by FDTD when the 3D model shown in FIG. 12 contains 1,000 dipoles.

When the number of the dipoles in the PMMA substrate is 1,000, the APD attains 800,000, which is $2\times10^5$ times higher than that without dipoles, as shown in FIG. 21.

Figure 22:
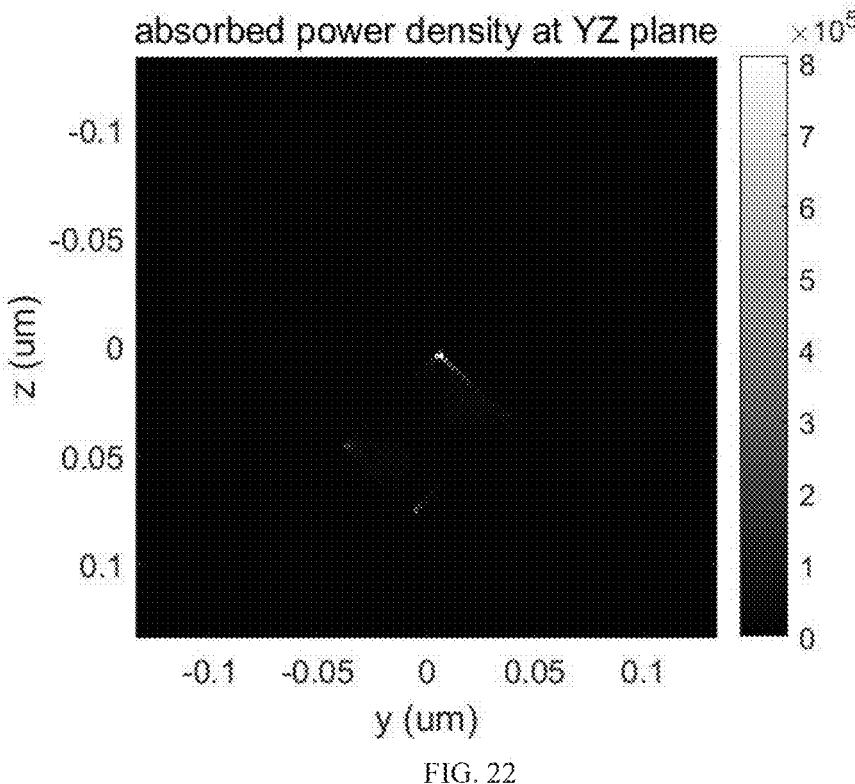
FIG. 22 shows the absorbed power density of the TiN nanocubes (45 nm) computed by FDTD when the 3D model shown in FIG. 12 contains 10,000 dipoles.
Figure 23:
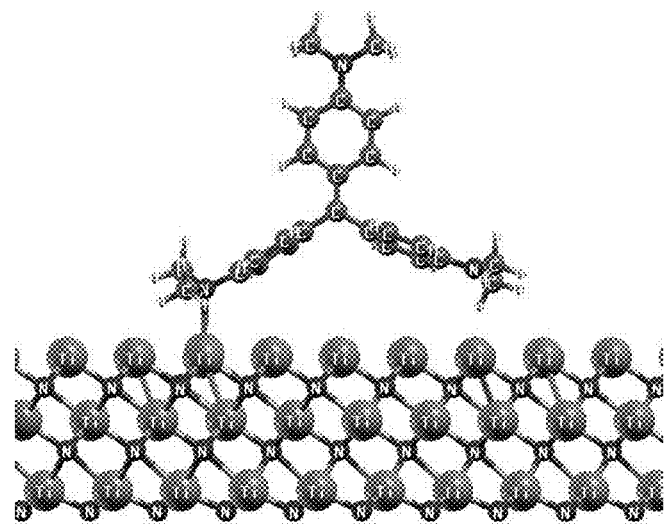
FIG. 23 shows the optimized configuration of crystal violet (CV_01) with N—Ti bonding formed on TiN(111) surface.
Figure 24:
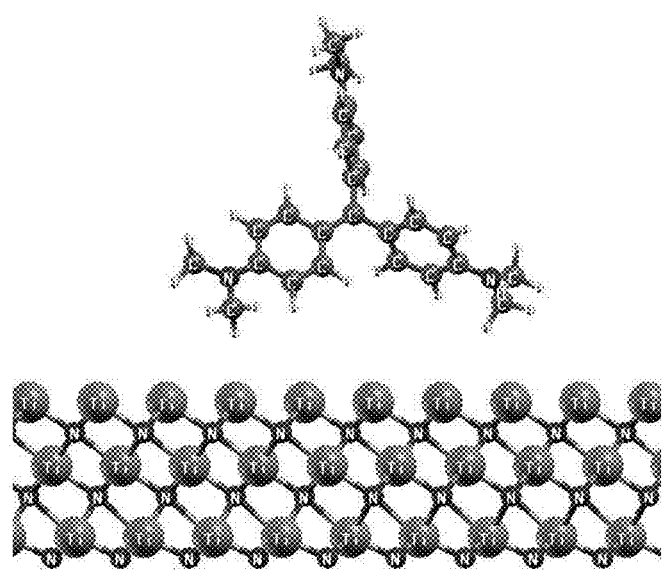
FIG. 24 shows the optimized configuration of crystal violet (CV_02) with N—Ti bonding formed on TiN(111) surface.
Figure 25:
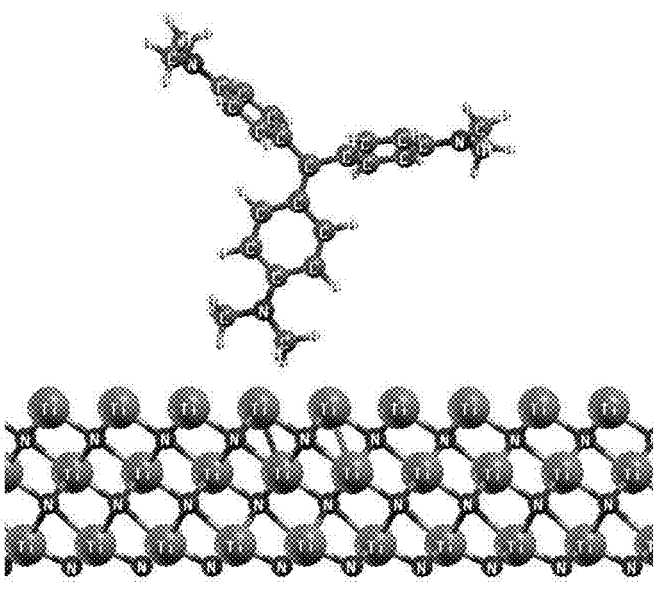
FIG. 25 shows the optimized configuration of crystal violet (CV_03) with N—Ti bonding formed on TiN(111) surface.
Figure 26:
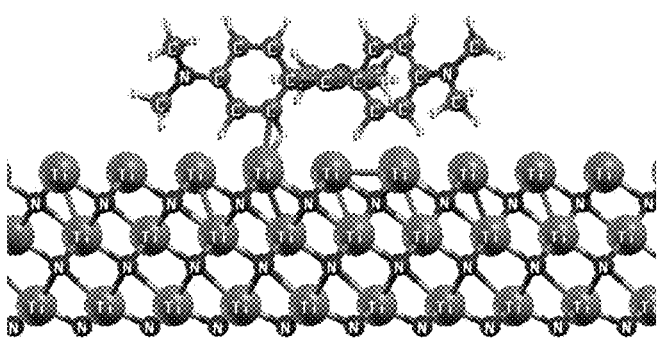
FIG. 26 shows the optimized configuration of crystal violet (CV_f) with N—Ti bonding formed on TiN(111) surface.

When the number of the dipoles in the PMMA substrate is 10,000, the APD attains 800,000, which is $2\times10^6$ times higher than that without dipoles, as shown in FIG. 22. The maximum APD has shifted to the utmost Z directions. This is a significant discover as high APD enables thermo-plasmonic effect to heat up the surrounding medium in close proximity to the TiN nanocube tip in the utmost Z direction.

Related patent (patent application No.: 202010930678.5) has already proved that: the TiN nanocubes are self-assembled on the surface of the PMMA through Ti—O bonds.

Through calculation using density functional theory, the energy change of each adsorbed configuration can be obtained, so as to judge the configuration that has the most chance to occur. All density functional theory calculations were performed by using open-sourced Quantum Expresso (QE) package V6.7. The interaction between ions and electrons is represented by Perdew-Burke-Ernzerhoff (PBE) parameterization using an ultra-soft pseudo-potential (USPP) method and generalized gradient approximation (GGA). Grimme's DFT-D3 method was used to deal with the interaction of Van der Waals forces. All calculations used the standard solid state pseudopotential of each element. The convergence of kinetic energy cut-off is set as 55Ry and 440 Ry. The convergence threshold of $10^{-4}$ Ry/Borr for total energy and $10^{-3}$ Ry for total force were used.

Each crystal violet molecule has three benzene rings and three —NCH$_3$CH$_3$ functional groups, wherein three benzene rings are located in different planes respectively. Two benzene rings with dihedral angle of 173.426° are called CV_01, two benzene rings with dihedral angle of 147.147° are called CV_02, a benzene ring on an axis of symmetry is called CV_03, while a benzene ring in the direction of plane stacking is called CV_f.

In order to construct the TiN(111) surface, the primitive cell of TiN was fully variable-cell relaxed. Then, the TiN (111) surface was constructed by cubic 4×6×3 TiN supercell (12 Å×18 Å×4 Å) with a sufficiently vacuum slab of 25 Å built along the z axis to avoid interaction of duplicated images. For sampling the Brillouin zone, Monkhorst-Pack k-point was set as 4×4×1. The CV molecule was placed initially in the middle and on the top of the TiN slab with touching contact via different functional groups. The optimized configurations of different N—Ti bonded crystal violet (CV_01, CV_02, CV_03 or CV_f) formed on the obtained TiN (111) surface after full relaxation are shown in FIG. 23 to FIG. 26 respectively.

The following energy is computed by using the open-sourced Quantum Expresso (QE) package V6.7 via density functional theory. The calculation formula of the adsorption energy E a is as follows:

$$E_a = E_{slab+cv} - E_{slab} - E_{cv};$$

wherein, $E_{slab+cv}$ is the total energy of titanium nitride surface after crystal violet is adsorbed, $E_{slab}$ is the total energy of isolated titanium nitride surface, and $E_{cv}$ is the total energy of isolated crystal violet, all of which are in the ground state.

The adsorption energy of each case is given in Table 1 below, wherein the smaller the value of the adsorption energy, the more stable the adsorption configuration. Therefore, the bond configuration that produces the maximum negative adsorption energy is the preferred configuration.

TABLE 1

| | Adsorption energy of crystal violet (CV) on TiN (111) surface | | | |
| --- | --- | --- | --- | --- |
| | TiN (111) + CV_01 | TiN (111) + CV_02 | TiN (111) + CV_03 | TiN (111) + CV_f |
| E$_a$ (eV) | −1.03 | −0.38 | −0.35 | +0.62 |
| E$_a$ (kcal/mol) | −23.75 | −8.76 | −8.07 | +14.30 |

It can be seen from Table 1 that the CV molecule is preferred to adsorb on the TiN (111) surface via the configuration shown by CV_01, that is, the CV molecules attaches to the TiN(111) surface via N—Ti bonding. The flat stacking formation is energetically unfavorable as extra energy is required.

Therefore, with addition of CV dye molecules to the PMMA matrix, we expected better absorption of TiN nanocubes onto the waveguide than PMMA alone.

This embodiment provides a thermo-plasmonic biochip. The biochip includes:

a first component, including a first substrate, wherein the first substrate is provided with a sample inlet hole, a first recess and a sample outlet hole which are communicated in sequence, a bottom surface of the first recess is provided with a plurality of first flow cells at intervals, each first flow cell is internally provided with a longitudinally arranged first conical waveguide extending out of the first flow cell and located in the first recess, and titanium nitride nanocubes are arranged on a conical surface of the first conical waveguide through chemical bonds;

a second component, including a second substrate, wherein the second substrate is provided with a second recess, a bottom surface of the second recess is provided with a plurality of second flow cells at intervals corresponding to the first flow cells, each second flow cell is internally provided with a longitudinally arranged second conical waveguide corresponding to the first conical waveguide, the second conical waveguide extends out of the second flow cell and is located in the second recess, and titanium nitride nanocubes are arranged on a conical surface of the second conical waveguide through chemical bonds; and the first substrate, the second substrate, the first conical waveguide and the second conical waveguide are made of PMMA and crystal violet.

FIG. 27 shows a flowchart of a preferred embodiment of the manufacturing method of the above biochip. The method includes the following steps of:

(1) adding 4.08 g of crystal violet powder to 1,180 g of transparent PMMA resin and fully stirring the mixture;

(2) performing 3D printing with a precision of 25 μm to obtain a first part and a second part respectively;

wherein, the first part and the second part are respectively the first component and the second component not modified with the TiN nanocube above;

(3) rinsing with a mixed solution of 90% ethanol +10% pure water for 15 minutes, then heating up to 60° C. and curing with 365 nm ultraviolet light for 15 minutes;

(4) adding 100 μg/mL ethanol solution of TiN nanocubes to the conical surface of each conical waveguide, and drying with nitrogen to disperse and fix the ethanol solution of TiN nanocubes on the conical surface of the conical waveguide to obtain the first component and the second component; and (5) docking the first component with the second component.

Figure 28:
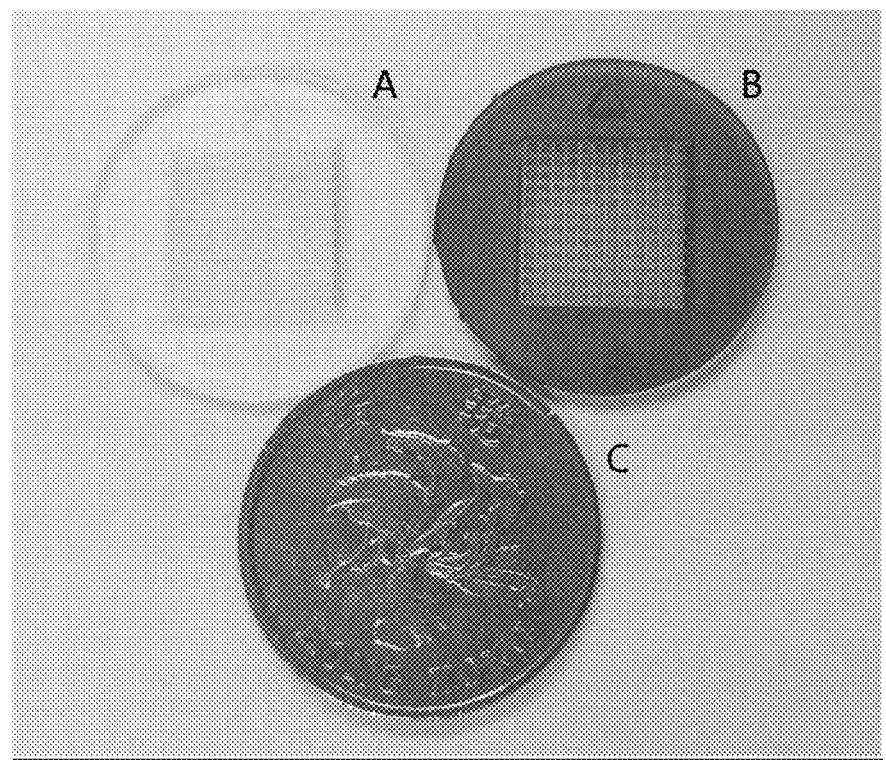
FIG. 28 shows a dimension comparison diagram of the biochip provided by the embodiment of the disclosure, wherein A is a biochip without crystal violet, B is a biochip with 10 mM crystal violet, and C is a Hong Kong SAR one dollar coin.
Figure 29:
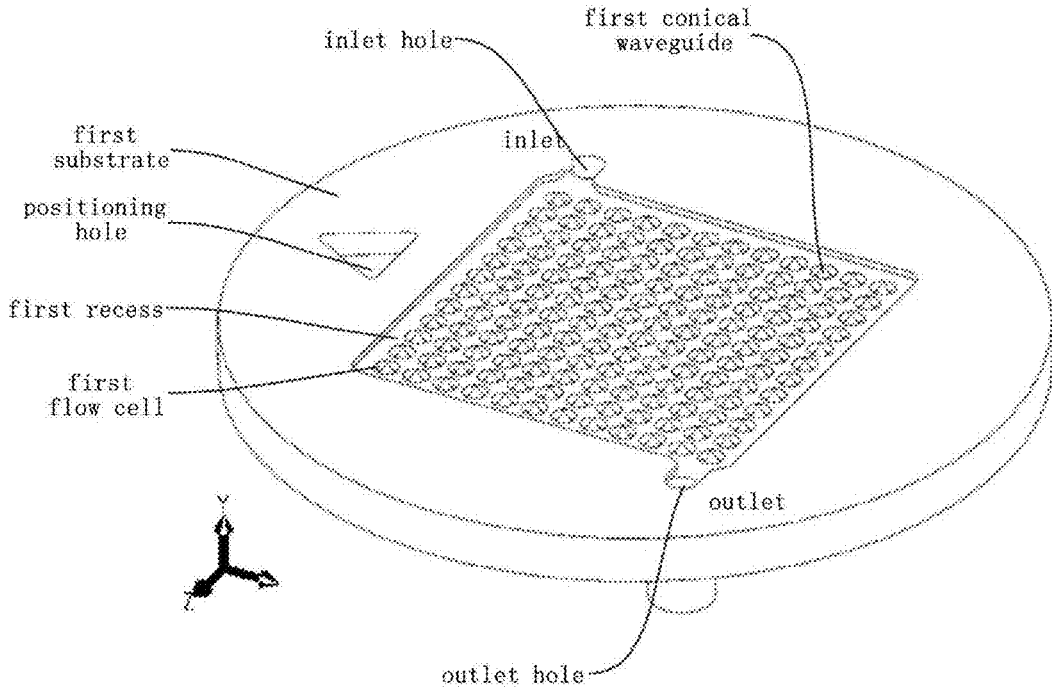
FIG. 29 shows a first component of the thermo-plasmonic tip-to-tip waveguide array with 144 nanofluidic wells provided by the embodiment of the disclosure.
Figure 30:
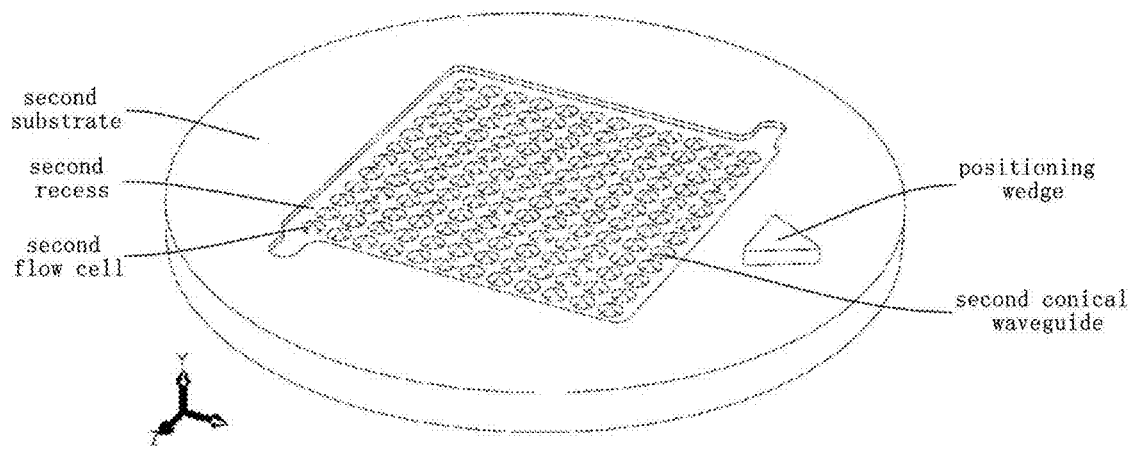
FIG. 30 shows a second component of the thermo-plasmonic tip-to-tip waveguide array with 144 nanofluidic wells provided by the embodiment of the disclosure.
Figure 31:
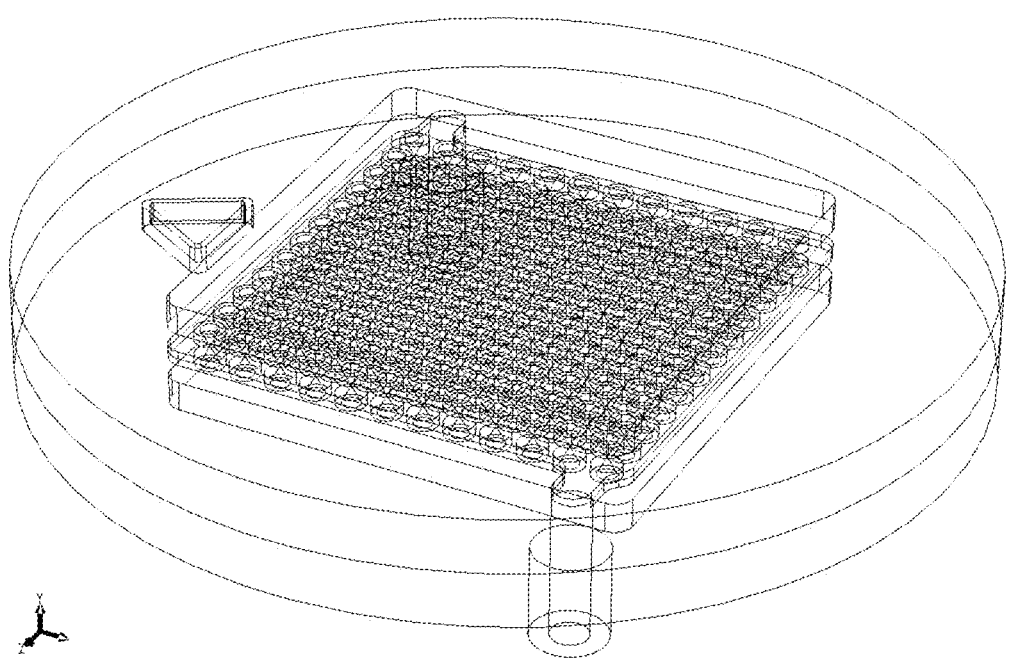
FIG. 31 shows the assembly of the first component shown in FIG. 29 and the second component shown in FIG. 30.

FIG. 28 shows a dimension comparison diagram of the biochip provided by the embodiment of the disclosure, wherein A is a biochip without crystal violet, B is a biochip with 10 mM crystal violet, and C is a Hong Kong SAR one dollar coin. FIG. 29 to FIG. 31 show a schematic implementation of the biochip (B) shown in FIG. 28.

Dimension parameters of the first component according to the schematic implementation of the biochip as shown in FIG. 29 are: 25 mm in diameter and 1.5 mm in thickness. Dimension of the first recess is 12×12×0.1 mm. There are 144 first flow cells distributed in a square array (12×12). The first flow cells are cylindrical, and each first flow cell has a bottom surface diameter of 800 μm and a height of 300 μm. The first conical waveguide with a bottom surface diameter of 125 μm and a height of 500 μm is longitudinally arranged in each first flow cell. Due to the first conical waveguide arranged in the first flow cell, the total fluidic sample volume that can be accommodated is reduced by almost ⅓, and the volume of the fluidic sample that can be accommodated in the first flow cell is about 100 nL.

Dimension parameters of the second component according to the schematic implementation of the biochip as shown in FIG. 30 are the same as that of the first component.

Figure 32:
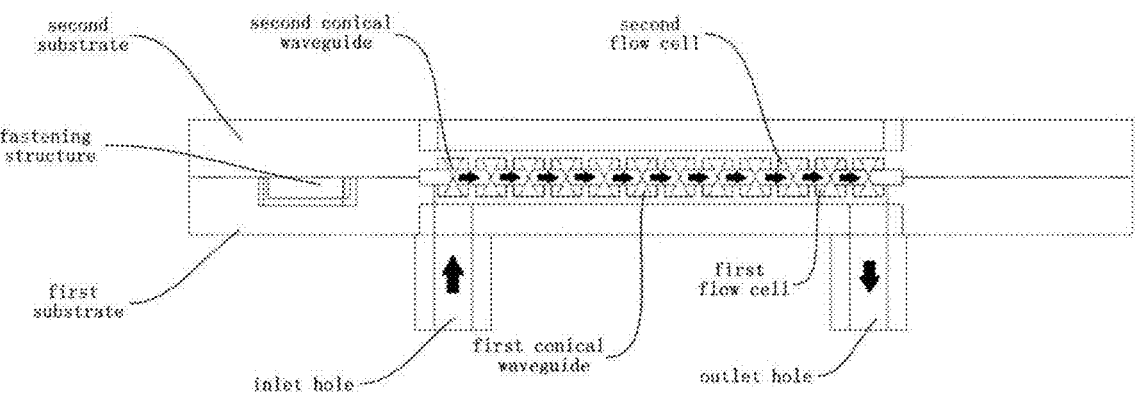
FIG. 32 is a sectional view of the assembly shown in FIG. 31.

The first component and the second component are combined to form the assembly shown in FIG. 31. A sectional view of the assembly is shown in FIG. 32, wherein the arrows indicate a flow direction of the fluidic sample.

Arrangement of the first component and the second component with two conical tip-to-tip waveguides arranged longitudinally is advantageous in that:

(1) the optical path of the probe beam can be increased by multiple total internal reflections;

(2) the absorbed power density can be increased by the focusing waveguide tip; and (3) the thermo-plasmonic heating efficiency can be improved by reducing the stagnant volume of the samples in the nanofluidic well.

The biochip provided by the embodiment further includes a fastening structure for fastening the first substrate and the second substrate.

Specifically, the fastening structure includes a positioning hole and a positioning wedge. The first substrate of the biochip provided in this embodiment is also provided with a positioning hole with a triangular cross section, as shown in FIG. 29. The second substrate is provided with a positioning wedge corresponding to the positioning hole above, and the positioning wedge are adapted in shape and dimension to the positioning hole, as shown in FIG. 30. The positioning wedge may be used to fix the first conical waveguide in the first component relative to the second conical waveguide in the second component, and assemble the biochip as shown in FIG. 31. It should be understood by those having ordinary skills in the art that the above-mentioned fastening structure is only for illustration, not limitation, as long as the first conical waveguide in the first component cab be fixed relative to the second conical waveguide in the second component to facilitate detection.

The volume of the fluidic samples in a reaction tank composed of the first flow cells and the corresponding second flow cells thereof is about 200 nL. Assuming aqueous buffer is used in the experiment as the fluidic sample medium and the specific heat capacity of water is known as 4.2 joules per gram per degree Celsius, the energy to increase the sample volume from 25° C. to 95° C. is calculated to be 0.059 joules. This is substantially less than the energy consumption of conventional PCR techniques which requires 50 microliters per sample, i.e., 14.7 joules for the same temperature increment.

Figure 33:
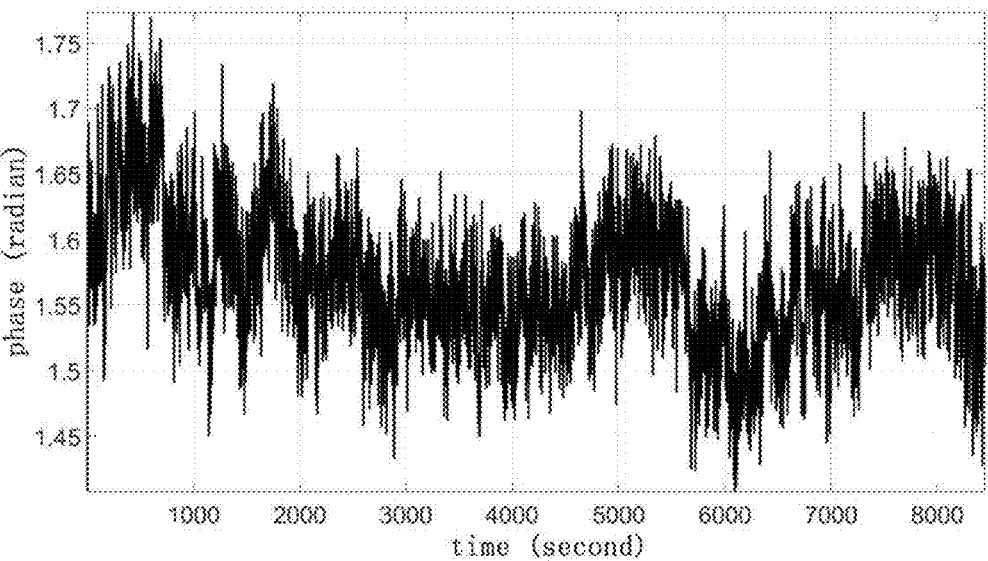
FIG. 33 shows experimental results of the thermo-plasmonic tip-to-tip waveguide array provided by the embodiment of the disclosure for detecting 10 pg/mL humanized C-reactive protein.

As shown in FIG. 33, the interaction between two biological molecules including a human CRP and an anti-human CRP (Beijing 4A Biotech Co., Ltd., catalog number CHE0104) were detected by using the biochip with crystal violet provided in the above embodiment. The chip was rinsed with phosphate buffer (PBS) from 0 seconds to 700 seconds. After 700 seconds, the CRP antibody with a concentration of 1:100 was injected at a rate of 30 μL/min, with a total injection amount of 500 μL. Then PBS was injected at 3,000 seconds to flush the excessive CRP antibody, and then 15 pg/mL human CRP standard was injected at 4,000 seconds. It was found that a phase change reaches 0.08 radian, the phase stability of the known measurement system reaches 0.002 radian, and the detection lower limit of the system can reach 0.3 pg/mL. Then, PBS was injected for washing at 5,500 second, and then human CRP standard with the same concentration of 15 pg/mL was injected at the same flow rate (30 μL/min) at 6,500 seconds, and the 590 nm LED light source was turned on to produce the thermo-plasmonic effect. It was found that the phase change was expanded to 0.16 radian, twice as large as before. Therefore, the detection lower limit of the biochip with crystal violet provided by the above embodiment can reach 0.15 pg/mL.

The embodiments of the disclosure are described in detail with reference to the drawings above, but the disclosure is not limited to the above embodiments, and various changes may also be made within the knowledge scope of those of ordinary skills in the art without departing from the purpose of the disclosure. In addition, in case of no conflict, the embodiments in the disclosure and the features in the embodiments may be combined with each other.

What is claimed is:

1. A thermo-plasmonic biochip, comprising:
a first component, comprising a first substrate, wherein the first substrate is provided with a sample inlet hole, a first recess, and a sample outlet hole, which are communicated in sequence, a bottom surface of the first recess is provided with a plurality of first flow cells at intervals, each first flow cell is internally provided with a longitudinally arranged first conical waveguide extending out of the first flow cell and located in the first recess, and a plurality of titanium nitride nanocubes are arranged on a conical surface of the first conical waveguide through chemical bonds;
a second component, comprising a second substrate, wherein the second substrate is provided with a second recess, a bottom surface of the second recess is provided with a plurality of second flow cells at intervals corresponding to the first flow cells, each second flow cell is internally provided with a longitudinally arranged second conical waveguide corresponding to the first conical waveguide, the second conical waveguide extends out of the second flow cell and is located in the second recess, and a plurality of titanium nitride nanocubes are arranged on a conical surface of the second conical waveguide through chemical bonds; and
wherein composition materials of the first substrate, the second substrate, the first conical waveguide, and the second conical waveguide contain PMMA and crystal violet;
wherein an amount of the crystal violet is 500 to 600,000 crystal violet molecules per cubic micron of the PMMA.

2. The thermo-plasmonic biochip of claim 1, wherein the first substrate and the second substrate allow light with a wavelength of 400 nm to 1000 nm to pass through.

3. The thermo-plasmonic biochip of claim 1, wherein heights of the first conical waveguide and the second waveguide are independently selected from 300 μm to 700 μm, respectively.

4. The thermo-plasmonic biochip of claim 1, wherein sizes of the first titanium nitride nanocube and the second titanium nitride nanocube are independently selected from 45 nm to 65 nm, respectively.

5. The thermo-plasmonic biochip of claim 1, wherein biochip further comprises a fastening structure comprising a positioning hole and a positioning wedge for fastening the first substrate and the second substrate, wherein the positioning hole is provided on the first substrate, and the positioning wedge is provided on the second substrate corresponding to the positioning hole.

6. The thermo-plasmonic biochip of claim 1, wherein the plurality of first flow cells is distributed in an array.

7. A manufacturing method of the thermo-plasmonic biochip of claim 1, comprising:

generating the first component and the second component which are not modified with the titanium nitride nanocubes by using the composition materials;

dispersing and fixing the titanium nitride nanocubes on the conical surfaces of the first conical waveguide and the second conical waveguide respectively to obtain the first component and the second component; and docking the first component with the second component.

8. The thermo-plasmonic biochip of claim 1, wherein the first substrate and the second substrate allow light with a wavelength of 500 nm to 800 nm to pass through.

9. The thermos-plasmonic biochip of claim 1, wherein the first substrate and the second substrate allow light with a wavelength of 550 nm to 650 nm to pass through.

10. The thermo-plasmonic biochip of claim 1, wherein heights of the first conical waveguide and the second waveguide are independently selected from 400 μm to 600 μm, respectively.

11. The thermo-plasmonic biochip of claim 1, wherein sizes of the first titanium nitride nanocube and the second titanium nitride nanocube are 45 nm.

12. The thermos-plasmonic biochip of claim 1, wherein an amount of the crystal violet is 70,000 to 85,000 crystal violet molecules per cubic micron of the PMMA.

13. A biosensing system, wherein the biosensing system comprises a thermo-plasmonic biochip comprising:

a first component, comprising a first substrate, wherein the first substrate is provided with a sample inlet hole, a first recess, and a sample outlet hole, which are communicated in sequence, a bottom surface of the first recess is provided with a plurality of first flow cells at intervals, each first flow cell is internally provided with a longitudinally arranged first conical waveguide extending out of the first flow cell and located in the first recess, and a plurality of titanium nitride nanocubes are arranged on a conical surface of the first conical waveguide through chemical bonds;

a second component, comprising a second substrate, wherein the second substrate is provided with a second recess, a bottom surface of the second recess is provided with a plurality of second flow cells at intervals corresponding to the first flow cells, each second flow cell is internally provided with a longitudinally arranged second conical waveguide corresponding to the first conical waveguide, the second conical waveguide extends out of the second flow cell and is located in the second recess, and a plurality of titanium nitride nanocubes are arranged on a conical surface of the second conical waveguide through chemical bonds; and wherein composition materials of the first substrate, the second substrate, the first conical waveguide, and the second conical waveguide contain PMMA and crystal violet;

wherein an amount of the crystal violet is 500 to 600,000 crystal violet molecules per cubic micron of the PMMA.

14. The biosensing system of claim 13, wherein the first substrate and the second substrate allow light with a wavelength of 400 nm to 1000 nm to pass through.

15. The biosensing system of claim 13, wherein heights of the first conical waveguide and the second waveguide are independently selected from 300 μm to 700 μm, respectively.

16. The biosensing system of claim 13, wherein sizes of the first titanium nitride nanocube and the second titanium nitride nanocube are independently selected from 45 nm to 65 nm, respectively.

17. The biosensing system of claim 14, wherein the biochip further comprises a fastening structure comprising a positioning hole and a positioning wedge for fastening the first substrate and the second substrate, wherein the positioning hole is provided on the first substrate, and the positioning wedge is provided on the second substrate corresponding to the positioning hole.

18. The biosensing system of claim 14, wherein the plurality of first flow cells is distributed in an array.

* * * * *